US009149035B2

(12) United States Patent
Percival et al.

(10) Patent No.: US 9,149,035 B2
(45) Date of Patent: Oct. 6, 2015

(54) ANTIMICROBIAL COMPOSITION

(75) Inventors: Steven L. Percival, Chester (GB); Phillip G. Bowler, Warrington (GB); David Parsons, Wirral (GB)

(73) Assignee: CONVATEC TECHNOLOGIES, INC., Reno, NV (US)

( * ) Notice: Subject to any disclaimer, the term of this patent is extended or adjusted under 35 U.S.C. 154(b) by 95 days.

(21) Appl. No.: 11/610,671

(22) Filed: Dec. 14, 2006

(65) Prior Publication Data

US 2007/0190176 A1    Aug. 16, 2007

(30) Foreign Application Priority Data

Dec. 14, 2005 (GB) .................................. 0525504.7

(51) Int. Cl.
*A01N 37/44* (2006.01)
*A01N 59/12* (2006.01)

(52) U.S. Cl.
CPC ............... *A01N 37/44* (2013.01); *A01N 59/12* (2013.01)

(58) Field of Classification Search
None
See application file for complete search history.

(56) References Cited

U.S. PATENT DOCUMENTS

| 4,258,056 A | 3/1981 | Lentsch |
| 4,829,129 A | 5/1989 | Kelley |
| 4,889,654 A | 12/1989 | Mason et al. |
| 5,340,924 A | 8/1994 | Tomita et al. |
| 5,407,656 A | 4/1995 | Roozdar |
| 5,616,347 A | 4/1997 | Alliger et al. |
| 5,744,155 A | 4/1998 | Friedman et al. |
| 5,998,488 A | 12/1999 | Shinohara |
| 6,413,556 B1 | 7/2002 | Bathurst et al. |
| 6,468,965 B1 | 10/2002 | Cutler |
| 2002/0160941 A1 | 10/2002 | Kruzel |

FOREIGN PATENT DOCUMENTS

| EP | 1158859 B | 5/2007 | |
| GB | 735462 A | 8/1955 | |
| WO | WO00/54593 | 9/2000 | |
| WO | WO 00/072874 | 12/2000 | |
| WO | WO01/37936 | 5/2001 | |
| WO | WO03047341 | 6/2003 | |
| WO | WO 03/068247 | * 8/2003 | ............. A61K 33/18 |
| WO | WO2004/028461 | 4/2004 | |
| WO | WO2004/035718 | 4/2004 | |
| WO | 2004/056346 | 7/2004 | |
| WO | WO2005/079582 | 9/2005 | |

OTHER PUBLICATIONS

Wirtanen, G., et al., Performance Evaluation of disinfectant Formulations Using Poloxamer-hydrogel Biofilm-constructs, Journal of Applied Microbiology, 1998, pp. 965-971, vol. 85.

(Continued)

*Primary Examiner* — Bethany Barham
*Assistant Examiner* — Barbara Frazier
(74) *Attorney, Agent, or Firm* — Wilson Sonsini Goodrich & Rosati

(57) ABSTRACT

An antiseptic composition suitable for use on skin and wounds comprising a source of an antimicrobial agent and an agent which disrupts biofilms. More, particularly the invention relates to a composition capable of providing effective antimicrobial activity while at the same time avoiding wound and skin irritation and retardation of wound healing.

6 Claims, 3 Drawing Sheets

(56) References Cited

OTHER PUBLICATIONS

Pennington, Jean, A Review of Iodine Toxicity Reports, Journal of the American Dietetic Association, Nov. 1990, pp. 1571-1581, vol. 90.

Lineaweaver, William, et al., Topical Antimicrobial Toxicity, Arch Surg., Mar. 1985, pp. 267-270, vol. 120.

Gilbert, P., et al., The Use of Poloxamer Hydrogels for the Assessment of Biofilm Susceptibility Towards Biocide Treatments, Journal of Applied Microbiology, 1998, pp. 985-990, vol. 85.

Poon, Vincent, et al., In Vitro Cytoxicity of Silver: Implication for Clinical Wound Care, Burns, 2004, pp. 140-147, vol. 30.

Database CA, Chemical Abstracts Service, Columbus, Ohio, US; Reybrouck, G., et al., "Effect of ethylenediaminetetraacetate on the germicidal action of disinfectants against Pseudomonas aeruginosa", XP002485721, STN-International Database Accession No. 72:11588.

Database CA, Chemical Abstracts Service, Columbus, Ohio, US; Izzat, I.N., et al., "Effect of varying concentrations of EDTA on the antimicrobial properties of cutting fluid preservatives", XP002485722, STN-International Database Accession No. 93:62380.

Database Medline, US National Library of Medicine, Bethesda, MD, 1988, Kaur, P., et al., "Effect of certain chelating agents on the antibacterial action of silver nitrate", XP002485723, Database Accession No. NLM3143759.

Database Biosis, Biosciences Information Service, Philadelphia, PA, 1992, Kida N., et al., "Effect of PH on Preferential Antibacterial Activity of Ethylenediaminetetraacetic Acid EDTA", XP002485724, Database Accession No. PREV199294118093.

Database Biosis, Biosciences Information Service, Philadelphia, PA, 2005, Percival, L., et al., "Tetrasodium EDTA as a novel central venous catheter lock solution against biofilm", XP002485725, Database Accession No. PREV200600021247.

\* cited by examiner

ANTIMICROBIAL COMPOSITION

This invention relates to an antimicrobial composition which can be applied to skin, wounds, cuts, abrasions or burns for the prevention or treatment of infections. More particularly, the invention relates to a composition capable of providing effective antimicrobial activity while at the same time avoiding wound and skin irritation and retardation of wound healing.

BACKGROUND OF THE INVENTION

Overuse of antibiotics and the associated increase in bacterial resistance is impacting the efficacy of antibiotics in the treatment of wound infection. Effective alternatives to antibiotics are thus desirable.

Topical antimicrobial materials, and preparations containing them, have long been recognized as playing an important part in minimizing the opportunity for skin and wound infections. Antiseptics are non-selective chemical agents that can be safe to use on living tissue. Molecular iodine, ionic silver and oxidizing agents, such as sodium hypochlorite and chlorine dioxide, have been recognized as antiseptic agents with effectiveness against a wide range of microorganisms. There are, however, several barriers to making an effective antimicrobial composition for application to wounds based on such agents. One problem is that these antiseptic agents tend to react with organic materials found in the wound other than the intended microbial targets. This means that to be effective, antiseptic agents need to be included in treatment compositions at high levels, which may cause undesirable side effects with prolonged use such as cell toxicity, hypersensitivity reactions, skin staining and systemic effects. Such side effects are further described in "In vitro cytotoxity of silver: implication for clinical wound care". Poon V K, Burd A. Burns. March 2004; 30(2):140-7, "A review of iodine toxicity reports". Pennington J A. J Am Diet Assoc. November 1990; 90(11):1571-81 and "Topical antimicrobial toxicity". Lineaweaver W, Howard R, Soucy D, McMorris S, Freeman J, Crain C, Robertson J, Rumley T. Arch Surg. March 1985; 120(3):267-70.

Wounds are often colonized by a variety of microorganisms, some of which may cause infection. It is increasingly recognized that microbial populations living within a biofilm environment contribute to delayed healing and infection. Biofilms are comprised of exopolymeric substances that are produced by bacteria once the bacteria attach to a surface, and this helps to protect microorganisms from immune cells and antimicrobial agents. Since efficacy of antimicrobial agents (e.g., antibiotics and antiseptics) is compromised by the biofilm matrix, strategies to disrupt the biofilm and expose microorganisms within can be helpful in increasing the activity level of antimicrobial agents and thus reduce the concentration of such agents needed to make an effective composition.

Ethylenediaminetetra-acetic acid (EDTA) added as the disodium or calcium di-sodium salts has been used to treat topical infections or to treat hard surfaces such as catheters. WO03/047341 describes the use of EDTA, for example, as an additive for a toothpaste. EDTA is also used as a formulation agent to reduce the effects of water hardness and, generally, as a chelating agent.

EDTA has been described in combination with other antibiotic agents. For example, in U.S. Pat. No. 5,998,488, EDTA is used in combination with an antimicrobial preservative in a solution for ophthalmic use. Formulations suitable for topical use on wounds have not been proposed.

There is, thus, a need for a composition which has the benefits of an antimicrobial agent but which reduces the potential of adverse reactions. Surprisingly, we have found that EDTA is capable of disrupting biofilms by chelating the metal ions, calcium and magnesium, that maintain the integrity of the biofilm matrix.

SUMMARY OF THE INVENTION

Accordingly, a first aspect of the invention provides an antimicrobial composition suitable for use on skin and wounds comprising a source of antiseptic agent and an agent which disrupts biofilms such as EDTA.

The presence of EDTA enhances the effect of the antiseptic so that the concentration of antiseptic agent may be reduced and yet still achieve effective antisepsis. By increasing the effectiveness of the antiseptic agent, its concentration in the composition can be reduced, thereby, reducing the potential for adverse reactions.

This aspect of the invention allows the preparation of compositions able to reduce the bacterial bioburden to a level manageable by the host within 24 hours using at least 50% less of the antiseptic agent, preferably 50-60% less, and, more preferably, 65-85% less. This then allows the wound to progress towards healing and can been evidenced by a visual improvement in the wound.

We have also found that it is possible to prepare a composition which includes EDTA which is effective under the conditions of pH normally found in a wound.

Accordingly, a second aspect of the invention provides a composition suitable for use on wounds comprising di-, tri- and tetra-basic salts of EDTA at a pH of 4 to 8.

DETAILED DESCRIPTION OF THE INVENTION

Figure 1:
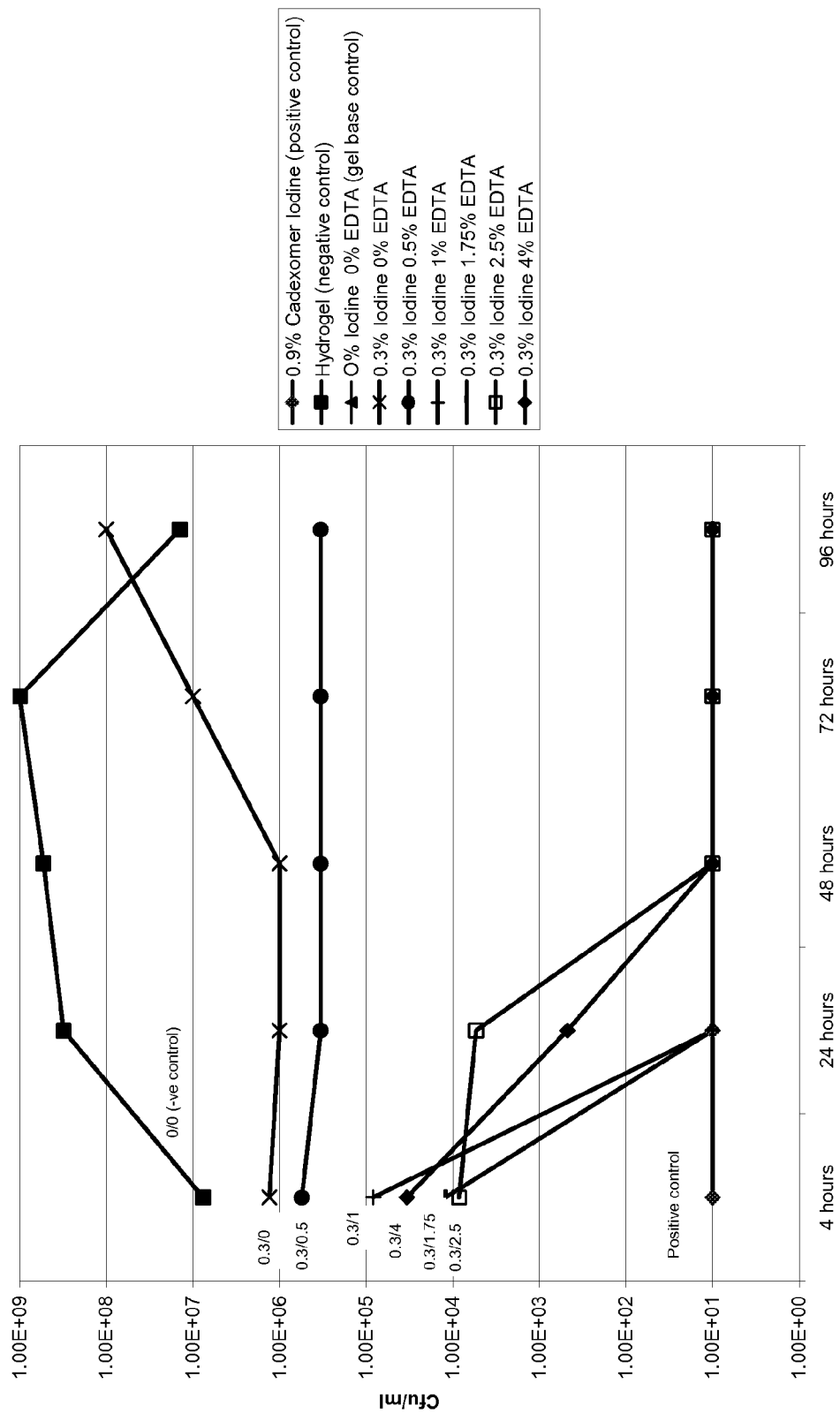
FIG. 1 is a graph showing the antimicrobial activity of a two component iodine generating solution with and without EDTA against *Staphylococcus aureus*.

The compositions according to a first aspect of the invention comprise an antiseptic agent, preferably molecular iodine, ionic silver, chlorhexidine, or hydrochloric acid or an oxidizing agent such as sodium hypochlorite, chlorine dioxide, hydrogen peroxide or peroxy acid salts. The antiseptic agent is preferably included in the composition at a level of from 0.01% to 10% by weight, more preferably 0.1% to 5% by weight. Iodine is preferably included in the composition at a level of from 0.01% to 10% by weight and more preferably from 0.1% to 1.0% by weight. Preferably, the source of iodine is an iodide and the composition further comprises an oxidant and a buffer, the oxidant being held separately from the iodide until the point of use. The buffer is preferably capable of maintaining the pH of the composition at between 4.5 and 6 so that iodine is generated at a physiologically acceptable and efficacious rate. Compositions comprising iodide and an oxidant held separately from the iodide are described further in EP1158859B.

Where iodide is present, the amount of oxidant in the composition is tailored to provide a stoichiometric match with iodide. Preferably, the oxidant is iodate and is provided in a molar ratio of from 1:4 to 1:10 with iodide. In this way, the iodide present in the composition fully reacts with the oxidant. Iodide and iodate are preferably present as sodium salts although other usual counter ions may be present.

Where the antiseptic agent is ionic silver, it is preferably included in the composition at a level of from 0.1% to 10% by weight and more preferably 0.5% to 1.5% by weight.

The pH of the composition is generally below 8 and preferably between 4 and 8, more preferably between 4 and 6 and most preferably between 4.5 and 5.5. The desired pH may be achieved by incorporating buffering agents in the composition. Examples of buffering agents which may be included are citric acid/di-sodium hydrogen phosphate, citric acid/sodium citrate, acetic acid/sodium acetate. The buffering agent may conveniently be present in an amount of about 1% to 20% by weight of the composition, preferably about 4% to 6% by weight and more preferably about 5% by weight so as to provide an isotonic composition EDTA is preferably present as the di-, tri- or tetra-basic salts of EDTA. We have found that these salts are effective for eradicating microorganisms in the free floating or planktonic state and biofilm state alone or in the presence of an antiseptic agent. For example, we have found that EDTA at concentrations of 0.1-40% weight by volume was effective in killing a range of microorganisms both in the planktonic and biofilm state. Microorganisms that were effectively killed by EDTA included *Pseudomonas aeruginosa*, *Serratia marcescens*, vancomycin resistant *Enterococcus* (VRE) and methicillin resistant *Staphylococcus aureus* (MRSA).

EDTA is preferably present in the compositions of either aspect of the present invention at a level of 0.5% to 10% by weight of the composition, more preferably 1% to 3% by weight.

The compositions of the present invention may be in the form of a water based gel which maintains a moist wound healing environment and promotes healing. A gel gives the advantage of flow into the wound to form an intimate contact with the wound bed and provide antimicrobial effects to the whole wound. Preferably, the gel has a high enough viscosity that it does not flow out of wounds on areas of the body that are or become non-horizontal. Preferably, the pH of the gel is buffered at around 5.5 as this does not alter the pH balance of the peri-wound tissue and, therefore, protects it.

The following examples are illustrative of the present invention.

Example 1

Effect of EDTA on Iodine

Compositions containing iodine and EDTA were prepared by making a pair of aqueous gels (see Table 1 for Gel A and Table 2 for Gel B) which were intimately mixed at the point of use. Each gel was made by preparing an aqueous solution containing all of the appropriate water-soluble parts according to the formulations below and then adding a slurry of a non-ionic cellulosic viscosifier (hydroxyethylcellulose) in propylene glycol.

TABLE 1

| Component | % w/w |
| --- | --- |
| Water | To 100 |
| Propan-1,2-diol | 10 |
| Hydroxyethylcellulose | 3.86 |
| Sodium iodate | 0.16 |
| Citric acid | 3.99 |
| di-sodium phosphate | 15.06 |

TABLE 2

| Component | % w/w |
| --- | --- |
| Water | To 100 |
| Propan-1,2-diol | 10 |
| Hydroxyethylcellulose | 4.14 |
| Sodium iodide | 0.59 |
| Ethylenediaminetetraacetic acid tetra-sodium salt tetrahydrate | 0.1-4.0 |
| Phosphoric acid | As necessary to adjust aqueous phase to ph 5.5 |

A commercially available cadexomer iodine ointment was present as a positive control as it contains 0.9% iodine. Intrasite is an amorphous hydrogel and was present as a negative control as it contains 0% iodine.

9 ml of simulated wound fluid was added to a 17 ml volume cell well. A 1 ml culture of *Staphylococcus aureus* was added to each well to give a final culture concentration of $10^6$ cfu/ml. Controls for this experiment involved adding 2 g of cadexomor iodine ointment (positive control) and nydrogel (negative control) separately to three cell wells each. 1 g of gels A and B, with different concentrations of EDTA, were then added to separate cell wells (in triplicate). The cell wells containing the culture and gels were then shaken at 600 rpm at 35° C. After time intervals of 4, 24, 48, 72 and 96 hours, a 0.1 ml test sample was taken from each well and placed into 9.9 ml MRD (maximum recovery diluent) containing 1% sodium thiosulphate. A 1 ml sample was then transferred to Tryptone Soy Agar plates and incubated for 48 hours. Bacterial counts were then recorded.

TABLE 3

| Test composition | 4 hours | 24 hours | 48 hours | 72 hours | 96 hours |
| --- | --- | --- | --- | --- | --- |
| Iodosorb(positive control) | 10 | 10 | 10 | 10 | 10 |
| Intrasite(negative control) | 7600000 | 310000000 | 530000000 | 1000000000 | 14000000 |
| 0% I$_2$ 0% EDTA | 7600000 | 310000000 | 530000000 | 1000000000 | 14000000 |
| 0.3% I$_2$ 0% EDTA | 1240000 | 1000000 | 1000000 | 10000000 | 100000000 |
| 0.3% I$_2$ 0% EDTA | 1010000 | 1000000 | 1000000 | 10000000 | 100000000 |
| 0.3% I$_2$ 0% EDTA | 1670000 | 1000000 | 1000000 | 10000000 | 100000000 |
| 0.3% I$_2$ 0.5% EDTA | 1500000 | 1000000 | 1000000 | 1000000 | 1000000 |
| 0.3% I$_2$ 0.5% EDTA | 92000 | 10 | 10 | 10 | 10 |
| 0.3% I$_2$ 0.5% EDTA | 58000 | 10 | 10 | 10 | 10 |
| 0.3% I$_2$ 1% EDTA | 8100 | 10 | 10 | 10 | 10 |

TABLE 3-continued

| Test composition | 4 hours | 24 hours | 48 hours | 72 hours | 96 hours |
|---|---|---|---|---|---|
| 0.3% I$_2$ 1% EDTA | 130000 | 10 | 10 | 10 | 10 |
| 0.3% I$_2$ 1% EDTA | 110000 | 10 | 10 | 10 | 10 |
| 0.3% I$_2$ 1.75% EDTA | 710 | 10 | 10 | 10 | 10 |
| 0.3% I$_2$ 1.75% EDTA | 4400 | 10 | 10 | 10 | 10 |
| 0.3% I$_2$ 1.75% EDTA | 31000 | 10 | 10 | 10 | 10 |
| 0.3% I$_2$ 2.5% EDTA | 8500 | 10 | 10 | 10 | 10 |
| 0.3% I$_2$ 2.5% EDTA | 10600 | 10 | 10 | 10 | 10 |
| 0.3% I$_2$ 2.5% EDTA | 6200 | 16000 | 10 | 10 | 10 |
| 0.3% I$_2$ 4% EDTA | 93000 | 10 | 10 | 10 | 10 |
| 0.3% I$_2$ 4% EDTA | 8500 | 10 | 10 | 10 | 10 |
| 0.3% I$_2$ 4% EDTA |  | 1400 | 10 | 10 | 10 |

The results shown in Table 3 are also shown graphically in FIG. 1.

These results show that by adding as little as 0.5% EDTA (calculated as the di-sodium salt) to iodine, the efficacy of iodine, at 0.3%, is enhanced when compared to the control of 0.3% iodine with no EDTA. Clearly, from the results, EDTA enhances the effects of iodine within 24 hours to the same efficacy of 0.9% iodine (positive control).

Example 2

Zones of Inhibition with Tetra Sodium EDTA

Seven antibiotic resistant microorganisms were used to evaluate the efficacy of EDTA in killing bacteria and yeasts grown on agar. For this experiment, filter paper discs were soaked in EDTA at concentrations ranging from 0.1-40%. EDTA was made up by dissolving it in an appropriate amount of sterile double distilled water. The filters were then added onto Muller Hinton agar which had been inoculated with a microorganism under study for 24 hours at 35° C. All microorganisms were tested twice.

Figure 2:
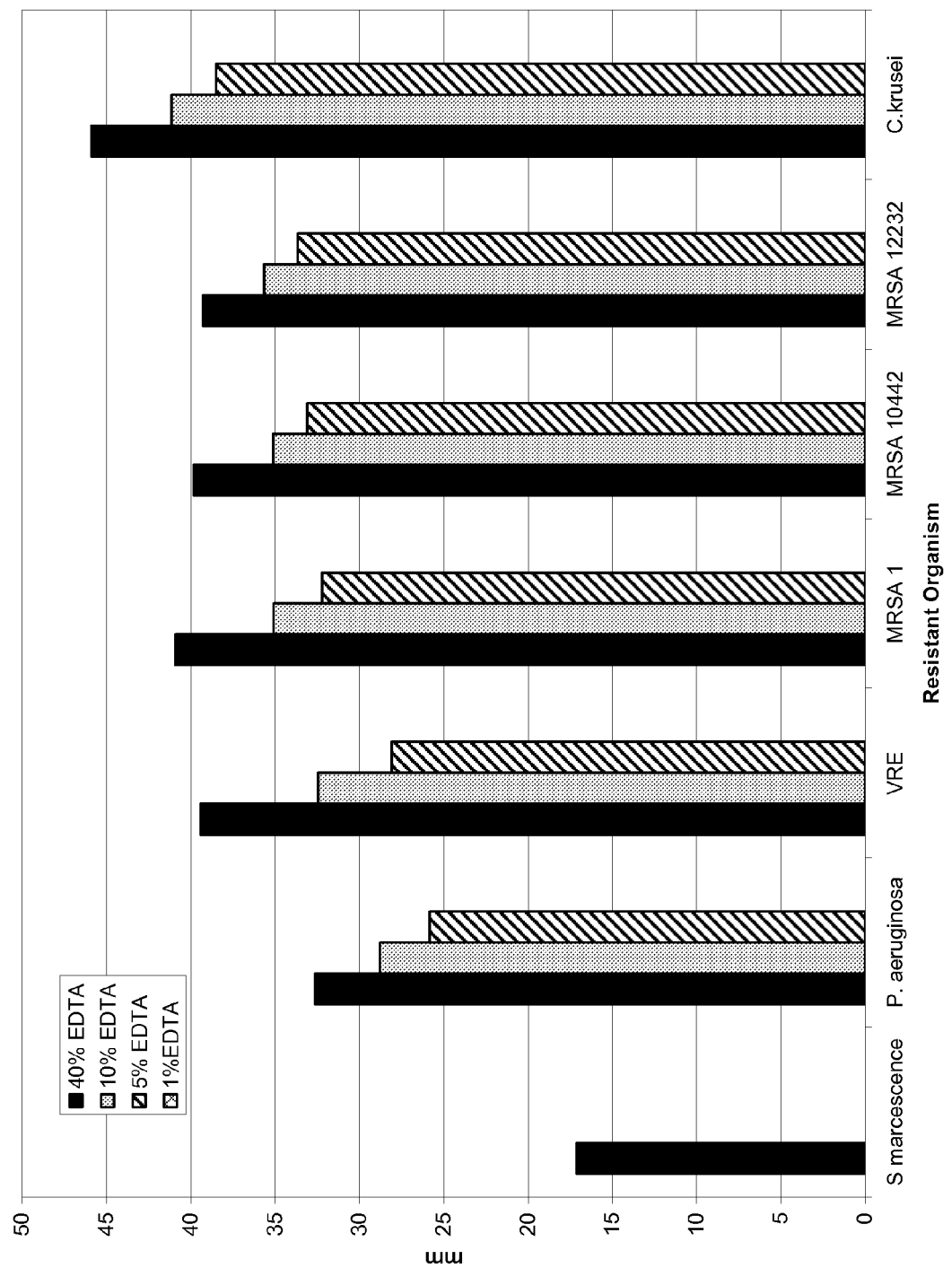
FIG. 2 is a graph showing zone of inhibition with EDTA.

The results in FIG. 2 show that the "zones of inhibition" generally ranged from about 20 to 43 mm (including disc 13 mm). Zones were higher with increasing levels of EDTA indicating that EDTA alone is an effective antiseptic agent.

Example 3

Zones of Inhibition with EDTA

Poloxamer F127 hydrogels (Univar, Basildon, Essex, UK) are di-block co-polymers of polyoxyethylene and polyoxypropylene that demonstrate thermo-reversible gelation properties. At temperatures below 15° C., poloxamer is liquid and fully miscible with water but changes to a firm gel at temperatures in excess of 15° C. Poloxamer encourages bacteria to exhibit a more clinically relevant biofilm phenotype. In *The Use of Poloxamer Hydrogels for the Assessment of Biofilm Susceptibility Towards Biocide Treatments*. Gilbert P., Jones, M. V., Allison, D. G., Heys, S., Maira, T., Wood, P. *Journal of Applied Microbiology* (1998; 85:985-990), Gilbert, et al., determined that *P. aeruginosa* cells grown on poloxamer hydrogel (biofilm form) express outer membrane proteins between 78 and 87 kDa, which are not evident in cells grown on standard nutrient agar ('planktonic'). Consequently, poloxamer gel cultures mimic many of the properties of biofilm-grown *P. aeruginosa* (Gilbert et al., 1998). This indicates that there is a phenotypic difference between *P. aeruginosa* cells grown on poloxamer hydrogel and nutrient agar, with only poloxamer grown cells resembling biofilm cells. It was found from Wirtanen's study (*Performance Evaluation of Disinfectant Formulations Using Poloxamer-hydrogel Biofilm-Constructs*. Wirtanen, G., Salo, S., Allison, D. G., Mattila-Sandholm, T., Gilbert, P. *Journal of Applied Microbiology* (1998; 85:965-971)) that bacteria which are grown in poloxamer have biofilm properties and associated enhanced biocide resistance. Gilbert and colleagues suggested that bacteria grown in poloxamer hydrogels could be exposed to biocides to provide a reproducible method for testing the antimicrobial efficacy of biocides against biofilm bacteria (Gilbert, et al., 1998).

Seven antibiotic resistant microorganisms were used to evaluate the efficacy of EDTA in killing bacteria and yeasts grown on poloxamer gel (biofilm state). For this experiment, filter paper discs were soaked in EDTA at concentrations ranging from 0.1-40%. In this present study, poloxamer F127, a di-block copolymer of polyoxyethylene and polyoxypropylene, was used as a medium on which bacteria could be grown as a biofilm phenotype and express the characteristics more appropriate to the 'real world'. The filters were then added onto Muller Hinton agar which had been inoculated with the microorganism under study for 24 hours at 35° C. All plates were done in duplicate.

Figure 3:
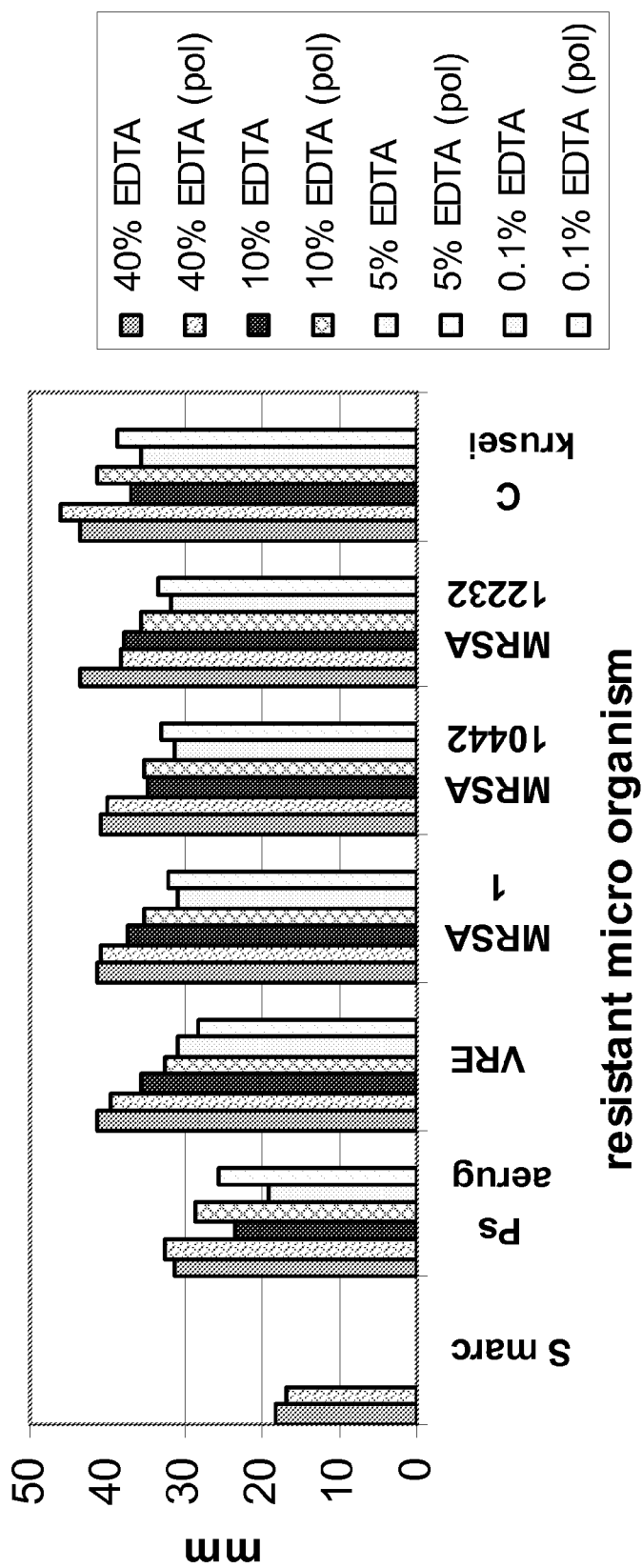
FIG. 3 is a graph showing zones of inhibition with EDTA, with and without poloaxmer.

The results in FIG. 3 show that the zones of inhibition were slightly smaller in the presence of poloxamer indicating that bacteria/yeasts growing as biofilms are physically more resistant to EDTA when compared to their planktonic couterparts. *C. kruzei* and *Ps aeruginosa* were the exception with larger zones with poloxamer. Zones of inhibition were evident on all organisms tested at 40% EDTA. At 10% EDTA and 5% EDTA there were no zones with *Serratia marcescens*. At 0.1% EDTA no zones of inhibition were evident with any organism studied indicating that EDTA is not effective at this level.

Example 4

Minimum Inhibitory Concentrations (MIC's) and Minimum Bactericidal Concentrations (MBC's) with Tetra, Tri and Di Basic Salts of EDTA A microtitre plate and optical density readings and visual inspection were performed to obtain the MIC's for a variety of microorganisms (see Table 4). Concentrations of EDTA included in this study were 40 mg/ml pH 10.00 as tetra-Na, 40 mg/ml as tri-Na pH 6.84, 40 mg/ml as di-Na pH 5.50. Into each microtitre plate, 100 µl of inoculum and EDTA was added. The plate was then incubated for 24 hours at 35° C.±3° C. Following incubation all microtitre plates were inspected visually for growth.

The results are presented in Table 4.

TABLE 4

| MICRO ORGANISM | IDENTIFICATION | IN-OCULUM cfu | MICs di Na | MICs tri Na | MICs tetra Na |
|---|---|---|---|---|---|
| S marcescens | multi res | 5.00E+04 | 0.938 | 1.875 | 0.938 |
| Ps aeruginosa | NCTC 8506 (res) | 6.75E+04 | 0.234 | 0.234 | 0.234 |
| Ps aeruginosa | NCIMB 8626 | 7.00E+04 | 0.938 | 0.938 | 0.938 |
| E coli | NCIMB 8545 | 5.50E+04 | 0.469 | 0.469 | 0.469 |
| E coli | NCIMB 10544 | <5.0+04 | 0.469 | 0.938 | 0.469 |
| Kl pneumoniae | 033 clinical isolate | <5.0+E4 | 0.938 | 0.938 | 1.875 |
| Ent cloacae | 166 clinical isolate | 5.00E+04 | 1.875 | 0.938 | 0.938 |
| Pr mirabilis | NCTC 9559 | 1.50E+05 | 0.469 | 0.469 | 0.469 |
| A baumannii | NCIMB 9214 | 4.40E+04 | 0.234 | 0.234 | 0.469 |
| S aureus | NCIMB 9518 | 4.00E+04 | 0.234 | 0.234 | 0.234 |
| MRSA | 1 Cardiff PHL | 5.50E+04 | 0.117 | 0.469 | 0.234 |
| MRSA | 2 Cardiff PHL | 5.75E+04 | 0.234 | 0.469 | 0.234 |
| MRSA | 26 | 1.25E+04 | 0.234 | 0.234 | 0.234 |
| MRSA | NCTC 12232 | 5.00E+04 | 0.234 | 0.234 | 0.469 |
| MRSA | NCTC 10442 | 6.50E+04 | 0.234 | 0.234 | 0.234 |
| MRSA | 103731 Chester PHL | 6.00E+04 | 0.234 | 0.117 | 0.234 |
| Ent faecalis | 141 clinical isolate | 2.50E+04 | 0.234 | 0.234 | 0.234 |
| VRE | 1 Cardiff PHL | 2.75E+04 | 0.234 | 0.469 | 0.234 |
| VRE | 2 Cardiff PHL | 3.25E+04 | 0.234 | 0.234 | 0.234 |
| VRE | NCTC 12201 | 6.00E+04 | 0.234 | 0.234 | 0.234 |
| Strep pyogenes | NCTC 8198 | 7.00E+04 | 0.234 | 0.469 | 0.234 |
| B subtilis | NCTC 3610 | 3.00E+04 | 0.234 | 0.234 | 0.234 |
| C krusei | NCPF 3876 (res) | 1.50E+04 | 0.938 | 0.938 | 0.938 |
| B fragilis | NCIMB 9343 | 1.90E+05 | 0.117 | 0.234 | 0.234 |
| Cl perfringens | 362 clinical isolate | 9.00E+03 | 0.117 | <0.117 | <0.117 |
| Pep anaerobius | NCTC 11460 | 1.30E+06 | 0.234 | 0.469 | 0.469 |

In general, all MIC's recorded were equivalent for all the salts of EDTA studied. This suggests that the pH of the solutions is equivalent. Therefore, the activity of EDTA is not affected by the salt form added to the microtitre plate. These results show that low concentrations of EDTA are very effective on bacteria.

Example 5

The Effect of EDTA on the Antimicrobial Efficacy of Silver Containing Wound Dressings The antimicrobial dressings used in this study were Acticoat™ (Smith and Nephew) and AQUACEL® Ag Hydrofiber® (ConvaTec). Acticoat is a nanocrystalline silver antimicrobial barrier dressing which consists of a rayon/polyester non-woven inner core laminated between two layers of silver-coated high density polyethylene mesh (HDPE). The layers are held together with ultrasound welds. AQUACEL® Ag is comprised of sodium carboxymethylcellulose Hydrofiber® and ionic silver. The silver cations in AQUACEL® Ag are associated with the individual highly absorbent anionic carboxymethylcellulose fibres of the Hydrofiber® dressing. AQUACEL® Hydrofiber® dressing (without silver) was also used as a control.

All dressings (AQUACEL® Hydrofiber® dressing [control—without silver], AQUACEL® Ag and Acticoat™ (nanocrystalline dressing) were hydrated with 20 mg/ml of tetra-Na EDTA. All tests were performed against Ps aeruginosa and tested on Mueller Hinton agar (MHA) and Poloxamer gel (incorporating Mueller Hinton broth (MHB). This involved inoculating either a MH agar plate or poloxamer gel plate with a specific isolate and then adding an appropriate hydrated (to saturation point) wound dressing (360 I (MRD) for AQUACEL® and AQUACEL® Ag and 150 I (sterile distilled water—as per manufacturers instructions) for Acticoat™). The plates were then incubated at 35° C.±3° C. for 24 hours after which the zone of clearance (no growth) around the dressing was measured. Zones of inhibition were measured horizontally and vertically (inclusive of the dressing sample) and a mean value was calculated from the duplicate set of results. The mean dressing size was then subtracted from the mean zone of inhibition to determine the corrected zone of inhibition (CZOI). A CZOI test allows for any inherent variability in the shape and size of zones created by the silver dressings which may change in dimension following hydration.

Table 5 shows the size of corrected zone of inhibition (CZOI) in mm on MH agar and poloxamer gel.

TABLE 5

| Hydrating Fluid | MHA (Non-biofilm bacteria) | | | Poloxamer gel with MHB (biofilm bacteria) | | |
|---|---|---|---|---|---|---|
| | AQUACEL | AQUACEL Ag | Acticoat | AQUACEL | AQUACEL Ag | Acticoat |
| EDTA | 0 | 16 | 10 | 6 | 6 | 7 |
| MRD | 0 | 18 | N/A | 0 | 3 | N/A |
| Water | N/A | N/A | 7 | N/A | N/A | 3 |

When EDTA was added to AQUACEL®, no zones of inhibition were observed on MHA (non-biofilm state). However, ZOI's were observed around AQUACEL® Ag on MHA (non-biofilm bacteria) when EDTA or (maximal recovery diluent) MRD was added indicating the antimicrobial activity of silver. Larger ZOI's were observed around Acticoat™ following the addition of EDTA when compared to hydration with water. In the presence of poloxamer gel an increase in the CZOI was observed following hydration of AQUACEL® Ag with MRD when compared to EDTA indicating an additive effect with the use of EDTA. Overall the results showed that EDTA enhances the effects of ionic silver on bacteria grown in the biofilm state (poloxamer gel). Overall these results suggest that by using an EDTA dressing it is effective against both planktonic and biofilm microorganisms.

Table 6 shows the size of corrected zone of inhibition in mm on MH agar and poloxamer gel.

TABLE 6

| Hydrating fluid | MHA (non-biofilm bacteria) | | | Poloxamer gel with MHB (biofilm bacteria) | | |
|---|---|---|---|---|---|---|
| | AQUACEL | AQUACEL Ag | Nano-crystalline silver dressing | AQUACEL | AQUACEL Ag | Nano-crystalline silver dressing |
| EDTA | 0 | 15.99 | 9.57 | 6.28 | 5.96 | 6.73 |
| MRD | 0 | 18.04 | N/A | 0 | 3.42 | N/A |
| Water | N/A | N/A | 6.74 | N/A | N/A | 2.82 |

Example 6
Minimum Inhibitory Concentrations (MIC) for a Two Component Gel Comprising Iodine and a Two Component Gel as Detailed in Example 1 Containing EDTA (diNa EDTA, triNa EDTA and tetraNa EDTA)

This experiment shows the effect of pH on the activity of a range of EDTA forms.

For this experiment a two component gel as detailed in Example 1 was made without the HEC component (gel). This experiment was therefore performed using only liquid compositions (see Table 7 for TCG Solution (A) and Table 8 for TCG Solution (B)) in order for MIC's to be calculated. The pH of the TCG/EDTA solutions was approx 5.5. The organisms tested included: *Staphylococcus aureus, Pseudomonas aeruginosa, Escherichia coli* (repeated twice) and *C. albicans*.

TABLE 7

| Component | % w/w |
|---|---|
| Water | To 100 |
| Sodium iodate | 0.1 |
| Citric acid | 3.99 |
| di-sodium phosphate | 15.06 |

TABLE 8

| Component | % w/w |
|---|---|
| Water | To 100 |
| Sodium iodide | 0.4 |
| Ethylenediaminetetraacetic acid tetra-sodium salt tetrahydrate | As shown in Table 1 |
| Phosphoric acid | As necessary to adjust aqueous phase to pH 5.5 |

Table 9 shows MIC's for TCG solution and TCG solution combined with EDTA (values in brackets are EDTA concentrations in mg/ml)

TABLE 9

| Bacterium | TCG solution* | TCG EDTA | TCG and tri Na EDTA | TCG and tetra Na EDTA |
|---|---|---|---|---|
| S aureus | 0.25 (0) | 0.008 (0.31) | 0.008 (0.31) | 0.008 (0.31) |
| Ps aeruginosa | 0.5 (0) | 0.062 (2.5) | 0.062 (2.5) | 0.062 (2.5) |
| E coli | 0.25 (0) | 0.031 (1.25) | 0.031 (1.25) | 0.031 (1.25) |

*(working concentration was 0.2% iodine)

MIC's were reduced considerably in the presence of EDTA (di, tri and tetra Na). It can be seen that the MICs, expressed as Iodine concentration, are lower in the presence of di, tri and tetra sodium EDTA.

The antimicrobial benefit of having EDTA present is achieved at concentrations of 0.31 mg/ml. Despite different forms of EDTA being known to provide differential antimicrobial efficacy, at a constant pH (5.5 in this case) all EDTA forms were equally effective in significantly reducing the MIC's for all three organisms compared to the iodine generating solution without EDTA.

We claim:

1. An antiseptic composition suitable for use on skin and wounds comprising 0.01% to 1.0% by weight of an antimicrobial agent comprising iodine, buffering agents to maintain the composition at a pH of about 4 to 6, and from 0.5% to 10% by weight of EDTA or its salts as an agent which disrupts biofilms, wherein the amount of iodine present in the composition is at a level of at least 50% less iodine than if EDTA were not present, such that the composition is able to reduce the bacterial bioburden present on the skin or wound to a level manageable by the host within 24 hours.

2. The antiseptic composition as claimed in claim 1 wherein the composition has a pH of between about 4.5 and 5.5.

3. The antiseptic composition as claimed in claim 1 wherein the composition is in the form of a gel.

4. The antiseptic composition as claimed in claim 1 wherein the iodine is provided by an iodine source, the iodine source is an iodide, and the iodide is held separately from the oxidant until the point of use.

5. The antiseptic composition as claimed in claim 4 wherein the composition is capable of generating from about 5 μg of iodine per gram of composition per hour to about 1500 μg of iodine per gram of composition per hour.

6. An antiseptic composition suitable for use on skin and wounds comprising buffering agents to maintain the composition at a pH of about 4 to 6, 0.01% to 1.0% by weight of iodine and from 0.5% to 10% by weight of EDTA or its salts as an agent which disrupts biofilms, wherein the amount of iodine present in the composition is at a level of at least 50% less iodine than if EDTA were not present.

* * * * *